US012778629B2

(12) United States Patent
Boudjema

(10) Patent No.: US 12,778,629 B2
(45) Date of Patent: Nov. 3, 2026

(54) DEVICE FOR LOADING HAIR GRAFTS INTO A GRAFT IMPLANTATION INSTRUMENT

(71) Applicant: Pascal Boudjema, Paris (FR)

(72) Inventor: Pascal Boudjema, Paris (FR)

(73) Assignee: Engraft Technologies, Inc., Marina Del Ray, CA (US)

( * ) Notice: Subject to any disclaimer, the term of this patent is extended or adjusted under 35 U.S.C. 154(b) by 671 days.

(21) Appl. No.: 17/210,386

(22) Filed: Mar. 23, 2021

(65) Prior Publication Data

US 2021/0315610 A1 Oct. 14, 2021

Related U.S. Application Data

(63) Continuation of application No. PCT/FR2019/000150, filed on Sep. 25, 2019.

(30) Foreign Application Priority Data

Sep. 27, 2018 (FR) ..................................... 18/58891

(51) Int. Cl.
*A61B 17/34* (2006.01)
*A61B 17/00* (2006.01)

(52) U.S. Cl.
CPC ..................... *A61B 17/3468* (2013.01); *A61B 2017/00752* (2013.01); *A61B 2017/00969* (2013.01); *A61B 2217/005* (2013.01)

(58) Field of Classification Search
CPC .......... A61B 17/3468; A61B 2217/005; A61B 2017/00752; A61B 2017/00969; A61B 2017/00561; A61F 2/10
See application file for complete search history.

(56) References Cited

U.S. PATENT DOCUMENTS 2,137,132 A 11/1938 Cooley ........................... 604/83
5,827,297 A * 10/1998 Boudjema .......... A61B 17/3417 600/564

(Continued)

FOREIGN PATENT DOCUMENTS

FR 2696334 4/1994
JP 2007-229330 9/2007

(Continued)

OTHER PUBLICATIONS

Preliminary Search Report and Written Opinion dated Mar. 15, 2019 in counterpart French Application No. 18/58891.

(Continued)

*Primary Examiner* — Brigid K Byrd
(74) *Attorney, Agent, or Firm* — Offit Kurman; Christopher I. Halliday; Chad Sayala

(57) ABSTRACT

The invention relates to a device (14, 14') for loading hair grafts into a Choi implanter-type implantation instrument, including an element comprising a first hole (18*a*) connected to a channel (17) that opens into a fluid-discharge chamber (21); a second hole (22) which can be connected to the fluid-discharge chamber (21) and define a path with the channel (17) such as to allow a needle (5) of an implantation instrument (1) to be introduced into the path through the second hole (22); and a connection means (23) for connecting the fluid-discharge chamber (21) to a vacuum source (27). The first hole (18*a*) is connected to a first tubing (20) used to deliver a graft (12) such that the graft (12) can be inserted into the needle (5) of the implantation instrument (1).

21 Claims, 8 Drawing Sheets

(56) References Cited

U.S. PATENT DOCUMENTS

| | | | | | |
|---|---|---|---|---|---|
| 5,989,279 | A * | 11/1999 | Rassman | A61B 17/3468 606/187 |
| 6,461,369 | B1 | 10/2002 | Kim | 606/187 |
| 6,572,625 | B1 * | 6/2003 | Rassman | A61B 17/32053 606/133 |
| 7,130,717 | B2 | 10/2006 | Gildenberg | G06F 19/00 |
| 7,452,367 | B2 | 11/2008 | Rassman et al. | 606/187 |
| 2002/0103500 | A1 | 8/2002 | Gildenberg | A61B 17/32 |
| 2004/0082915 | A1 | 4/2004 | Kadan | 604/164.04 |
| 2004/0193203 | A1 * | 9/2004 | Pak | A61B 17/3468 606/187 |
| 2006/0293703 | A1 | 12/2006 | Pak et al. | A61B 17/34 |
| 2007/0106306 | A1 * | 5/2007 | Bodduluri | A61B 34/70 606/133 |
| 2008/0050805 | A1 * | 2/2008 | Cole | A61B 10/0096 435/289.1 |
| 2013/0096600 | A1 | 4/2013 | Wesley et al. | A61B 17/34 |
| 2014/0343575 | A1 * | 11/2014 | Andreani | A61B 17/32053 606/132 |
| 2015/0209786 | A1 | 7/2015 | Hage et al. | B01L 3/00 |
| 2017/0065291 | A1 * | 3/2017 | Lewallen | A61B 17/32053 |
| 2017/0143434 | A1 | 5/2017 | Jung | A61B 34/30 |
| 2018/0221054 | A1 * | 8/2018 | Truckai | A61B 17/00234 |

FOREIGN PATENT DOCUMENTS

| | | |
|---|---|---|
| JP | 2009-509671 | 3/2009 |
| JP | 2009-279430 | 12/2009 |
| JP | 2014-534008 | 12/2014 |
| JP | 2017-515640 | 6/2017 |
| KR | 10-2017-0056058 | 5/2017 |
| WO | 2007/041267 | 4/2007 |
| WO | 2015/186146 | 12/2015 |

OTHER PUBLICATIONS

Preliminary Search Report and Written Opinion dated Mar. 30, 2021 in counterpart International Application No. PCT/FR2019/000150 and English translation thereof.

"Thermo Scientific Matrix Microplate Data Sheet", Thermo Fisher Scientific Inc., Jan. 1, 2008 (Jan. 1, 2008), pp. 1-19, XP055250751, URL: https://tools.thermofisher.com/content/sfs/brochures/D17414.pdf.

Niw Surgicals: "FUE Implanter Pen (Choiz Types), NIW-IMP11—Hair Transplant, Hair Transplant And Restoration", Jan. 3, 2018 (Jan. 3, 2018), XP055887310, URL: https://www.indiamart.com/proddetail/fue-implanter-pen-choiz-types-niw-impll-hair-transplant-17852228888.html.

Office Action dated May 31, 2022 in counterpart Japanese Application No. 2021-542278, together with English translation thereof.

Extended European Search Report dated Aug. 11, 2022 in counterpart European Application No. 22153104.9, together with English translation thereof.

CNOA, US2004/0082915A1, Yes—IDS Jul. 2, 2021.

CNOA, CN1318992A, No, U.S. Pat. No. 6,461,369 (B1)—IDS Jul. 2, 2021 WO0110307 (A1).

CNOA, CN1589748A, No, US2005/0096687 (A1) U.S. Pat. No. 7,452,367 (B2)—IDS Jul. 2, 2021.

CNOA, U.S. Pat. No. 6,461,369 B1, Yes—IDS Jul. 2, 2021.

ILOA, US2004/0082915A1, Yes—IDS Jul. 2, 2021.

Office Action dated Dec. 27, 2023 in counterpart Israel Application No. 281800, together with English translation thereof.

Office Action dated Nov. 10, 2023 in counterpart Chinese Application No. 201980068767.9, together with English translation thereof.

Office Action dated Aug. 26, 2024 in counterpart Korean Application No. 10-2021-7012533, together with English translation thereof.

Office Action dated Nov. 26, 2024 in counterpart Korean Application No. 10-2021-7012533, together with English translation thereof.

Office Action dated May 28, 2025 in counterpart Korean Application No. 10-2021-7012533, together with English translation thereof.

Office Action dated Sep. 11, 2025 in counterpart Brazilian Application No. BR112021005838-9, together with English translation thereof.

* cited by examiner

Fig. 10
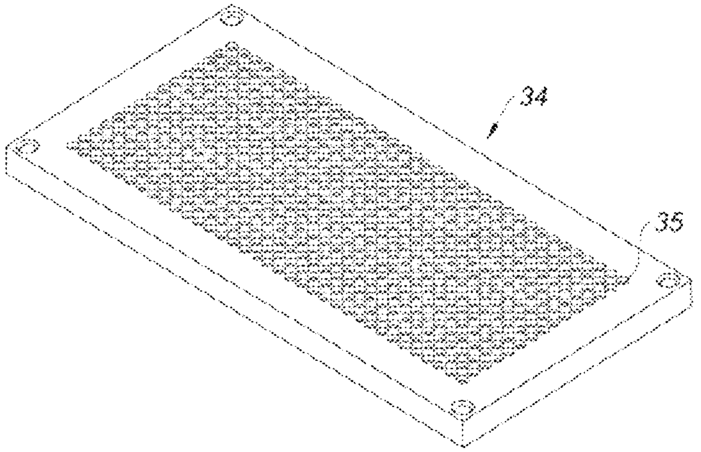
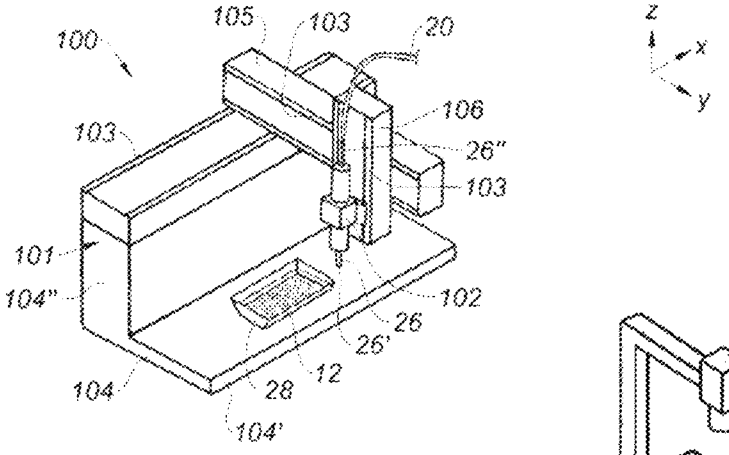
Fig. 11
Fig. 12
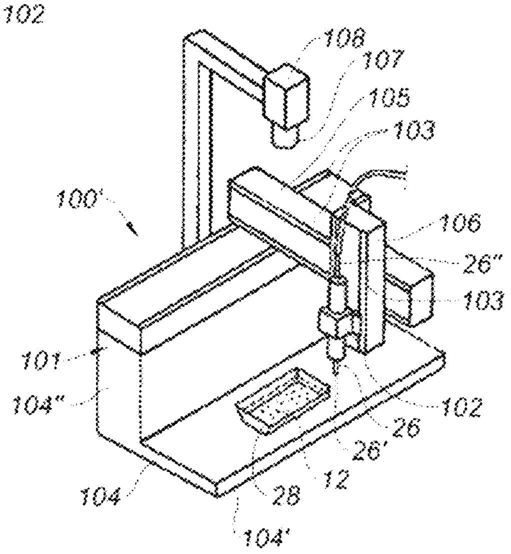

DEVICE FOR LOADING HAIR GRAFTS INTO A GRAFT IMPLANTATION INSTRUMENT

CROSS-REFERENCE TO RELATED APPLICATIONS

The present application is a continuation of International Patent Application No. PCT/FR2019/000150 filed Sep. 25, 2019, which claims the benefit of priority from French Application No. 18/58891 filed Sep. 27, 2018, the content of all of which are incorporated by reference as if set forth in full herein.

BACKGROUND

Technical Field

This invention concerns a device for loading hair grafts into an instrument for implanting said grafts into the skin, and a method for the transfer and loading of hair grafts into an instrument for implanting said grafts into the skin.

Description of Related Art

The present invention has a particularly important, though not exclusive, application in the field of surgical treatment of baldness by hair transplant.

A known hair transplant technique consists of taking skin fragment samples from the back of the scalp, generally in cylindrical form and of very small diameter called grafts or micro grafts, comprising generally one to three hair roots called follicular units, loading them into an instrument for implantation and reimplanting them in bald zones.

Graft cutting devices comprising a means of cutting the skin comprising an open-end, circular and sharp, hollow, needle-type punch mounted on a handle, are a known graft capture device. This type of punch is called a micro punch. It can be manual or have an electric rotary motor actuated by an operator.

The graft capture procedure using this type of device consists in placing the micro punch in front of the graft to be removed, where the hair has been previously cut to approximately one millimeter in length, then pushing the micro punch into the scalp a few millimeters deep by a rotational movement, following the emergence axis of the graft hair. The micro punch is then removed from the scalp and the precut graft is extracted from the scalp by traction with the use of very thin tweezers, before being placed in a tank containing a preservation solution. The hair graft can then be loaded into an implanting instrument in order to be reimplanted in balding or bald zones.

Loading the hair graft into a Choi Implanter-type implanting instrument, as described in the FIGS. 1A, 1B, and 2, is usually carried out manually. The hair graft is seized manually between the jaws of a pair of thin tweezers held by an operator, then inserted into the hollow needle of said instrument through a longitudinal slot in the needle.

SUMMARY

It is easily understood that this manual step of loading the hair graft into the implant needle is a long and delicate maneuver requiring extreme precision that prolongs the operation time. Indeed, the implanting instrument needle is generally made of stainless steel, and has very small dimension: 10 millimeters in length on the free part protruding from the implanting instrument, an outside diameter in the range of 0.7 to 1 millimeter, and a very thin wall thickness of 0.1 millimeter. Thus, it is necessary for the operator to correctly visualize and position the slot in order to very delicately, manually insert the hair graft.

Furthermore, a minute portion of the hair graft may be outside of the needle, through the slot, and may thus be damage or severed by strangulation in the slot due to its narrowness when positioned inside the needle. This results in rendering the hair graft improper for transplant. Changing hair grafts is then required.

In certain cases, hair graft removal can be carried out with the help of a vacuum extraction system, comprising a cutting device as previously described. This vacuum extraction system comprises a tubing connected to the cutting device in a sealed manner, and connected to a tank containing a preservation solution and vacuuming means for the tubing.

Implanting hair grafts into bald zones is usually carried out in two different manner: direct and indirect implantations.

In indirect implantation, the hair grafts are inserted one by one into previously-made micro incisions in the bald skin. Hair graft insertion is usually done manually by using micro tweezers.

In direct implantation, the hair grafts are directly injected into the bald skin, by using an implanting instrument, without requiring prior micro-incisions. The implanting instrument the most commonly used, as described in the patent application U.S. Pat. No. 6,461,369 called "Choi Implanter", is composed of a body with an extending, hollow, retractable cylindrical needle on the beveled, sharp, open end in which the hair graft to be implanted into the scalp is positioned. A sliding rod within the needle allows the release and maintaining of the hair graft in the scalp when withdrawing the needle into the implanting instrument. The needle is remarkable in that it has a longitudinal narrow opening or slot for manually loading the hair graft by retrofit, using very thin tweezers.

Such an implanting instrument has the advantage of no longer requiring the previous realization of numerous micro incisions to the skin in the bald zone, but unfortunately presents several inconveniences. Indeed, the manual loading of the hair graft is long, delicate, tedious, and traumatizing to the hair graft whose head, previously seized by a tweezer, is strangled by the edges of the needle's narrow slot. In this manner, the head of the hair graft may be amputated and thus become improper for transplant. Furthermore, it is often necessary to have a qualified staff of at least two operating assistants whose sole task consists of placing the hair grafts into several implanting instruments, on a table, that are manually and successively exchanged with the main operator in charge of the implanting itself of the hair grafts into the scalp. It is thus necessary to have a large number of implanting instruments to load in order to optimize the implantation operation time. These long and delicate manipulations also increase the risk of accidental injury of the operators during the exchange of instruments.

A known solution consists of capturing and loading the hair grafts into an implanting instrument in one step. This solution is described in the patent FR 2 696 334 that presents a hair graft cutting device connected to an implanting instrument by tubing.

Another solution described in the patent U.S. Pat. No. 7,452,367 consists of loading the hair grafts positioned, for example in a tank containing a preservation solution, into an implanting instrument having a hole connected to a vacuum tubing. In this way, the loading of the hair grafts into the implanting instrument eliminates the need for manual loading of the implanting instrument needle.

However, these solutions are not compatible with the existing "Choi Implanter"-style implanting instruments. Indeed, implanting instruments as described in the patents FR 2 696 334 and U.S. Pat. No. 7,452,367 have, contrary to Choi Implanters, holes allowing their connection to channels or tubing enabling, among other things, the suction of a hair graft by vacuum suction.

The present invention has for one object to resolve the inconveniences listed above by offering a device for loading hair grafts into a Choi Implanter-type implanting instrument, allowing simple and quick loading of hair grafts into the implanting instrument, safely and without trauma, reducing labor costs without requiring a modification of the structure of the implanting instrument, and a loading procedure for a Choi Implanter-type implanting instrument using such a hair graft loading device.

One purpose of the present invention is to eliminate the delicate manipulations and the inconveniences listed above by proposing a device more adapted to use that allows the quick and easy loading of a hair graft into a Choi Implanter-type implanting instrument, safely and without trauma.

For this purpose, the invention proposes a device for loading hair grafts hair grafts into a Choi Implanter-type implanting instrument, characterized in that it has an element comprising: a first hole connected to a channel leading into a fluid-discharge chamber; a second hole capable of communicating with the fluid-discharge chamber and defining a path with the channel, in such a way as to allow the insertion of the needle of the implanting instrument into said path through the second hole; a connection means from the fluid-discharge chamber to a vacuum source; the first hole being intended to communicate with the first tubing intended to deliver a hair graft, in such a way that the hair graft can be inserted into the needle of the implanting instrument.

In that respect, the device for loading the hair graft according to the invention has numerous advantages in regard to prior art. It saves a considerable amount of time during handling and it is no longer necessary to have a large number of manually, precharged, implanting instruments. One single implanting instrument can suffice to carry out the intervention, which represents a significant economic gain.

Furthermore, it is no longer necessary to worry about the correct positioning of the slot of the needle of the implanting instrument while loading the hair graft into the needle of said instrument, given the fact that once the latter is inserted into the hair graft loading device according to the invention, the open part of the slot freely communicates with the fluid-discharge chamber, laterally, at 360° around its axis. Loading is ensured during the vacuuming of the fluid evacuation chamber.

Moreover, loading an implanting instrument using the device according to the invention can be carried out by one operator using the same instrument, which has for effect to prevent any risk of accidental puncture thanks to the absence of the physical exchange of instruments between different operators.

According to other characteristics of the invention, the invention device comprises one or more of the following optional characteristics, taken alone or in any combination.

According to one characteristic, the fluid-discharge chamber has dimensions such that it is able to allow both a passage of fluid, such as air or water, between the channel and the connection means from the fluid evacuation chamber to a vacuum source, and loading a hair graft into the needle of a Choi Implanter-style implanting instrument inserted into the channel via the second hole.

According to a characteristic, the channel is rectilinear.

According to another characteristic, the connection means from the fluid evacuation chamber to a vacuum source is a vacuum conduit positioned in the hair graft loading device, substantially parallel to the channel, intended to be connected to the vacuum source by an outlet orifice.

As a variant, the connection means from the fluid-discharge chamber to a vacuum source is a vacuum conduit positioned laterally and perpendicularly to the channel.

According to an embodiment, the hair graft loading device has a substantially cylindrical form with a proximal side, a distal side, and a longitudinal side connecting the proximal and the distal sides.

According to this embodiment, the proximal side comprises the second holes and the distal side comprises the first hole of the channel.

Still according to this embodiment, in the variant according to which the connection means from the fluid evacuation chamber to a vacuum source is a vacuum conduit positioned in the hair graft loading device, substantially parallel to the channel, intended to be connected to the vacuum source by an outlet orifice, the outlet orifice of the vacuum conduit is positioned on the distal side of the hair graft loading device.

As a variant, the outlet orifice of the vacuum conduit is positioned laterally, on the longitudinal side of the hair graft loading device.

The first hole of the channel is advantageously positioned in the center of the distal side of the hair graft loading device.

According to this characteristic, the second holes of the channel is positioned in the center of the proximal side of the hair graft loading device.

Thus, the first and second holes are aligned in the axis of the channel, or coaxial.

The hair graft loading device preferentially comprises connection means from the tubing, enabling the remote connection of respectively the channel to a hair graft tank and the conduit to a vacuum source.

The invention further concerns a method of using the device as described above for loading a hair graft into a Choi Implanter-type implanting instrument, comprising the following steps: connecting a first tubing to the first hole, via a means of connection, introducing the needle of the implanting instrument, in a sealed manner, into the second hole, in such a manner that it penetrates into at least one part of the channel, bringing the open end of the first tubing into contact with a hair graft located in a solution in a tank or container, and vacuum sealing the fluid-discharge chamber.

The invention also concerns a hair graft storage tray configured to facilitate the suction of a hair graft into the hair graft loading device as described above, the storage tray comprising at least one well configured to contain a hair graft and whose dimensions allow the maintenance of the hair graft in a given position, adapted to allow the suction of the hair graft into the hair graft loading device as described above.

In this way, when a hair graft is inserted into the well with its epidermic portion close to the opening of the well, the hair graft is maintained in this position, so that the hair graft can be easily sucked into the hair graft loading device.

According to one characteristic, the well has a diameter of 1.5 mm and a depth of 8 mm.

According to one characteristic, the storage tray comprises a plurality of wells aligned in several rows, equidistant from each other and spaced at approximately 5 mm.

The invention concerns a hair graft suction device configured to suck a hair graft into the hair graft loading device as described above.

The hair graft suction device is a robot comprising a support and a housing for a rigid tube configured to be connected to the first tubing of a hair graft loading device as described above, the housing being mobile in relation to the support and configured to be moved in order to position the rigid tube to come into contact with a hair graft.

According to one characteristic, the housing is mobile along three orthogonal axes, relative to the hair graft storage tray.

According to one characteristic, the suction device further comprises: a camera configured to record an image of a hair graft located in a container, and a controller configured to analyze the precise position of the hair graft.

The invention concerns an assembly comprising a hair graft loading device and a hair graft suction device as described above.

The invention concerns an assembly comprising a hair graft loading device, a hair graft suction device, and a storage tray, as described above.

The invention will be better understood by reading the embodiments given below as non-limiting examples.

BRIEF DESCRIPTION OF THE DRAWINGS

The description refers to the Drawings that accompany it wherein:

FIG. 10 is a perspective view of an embodiment of a hair graft storage tray according to the invention;

FIGS. 11 and 12 are perspective views of two embodiments of a hair graft suction device according to the invention;

DETAILED DESCRIPTION

In the description and in the claims that follow, identical, similar or analogical components will be referred to by the same reference numbers and we will use the terms "front", "back", "horizontal", "vertical", "upper", "lower", etc. on a non limiting basis and in reference to the Drawings in order to facilitate the description.

Figure 1A:
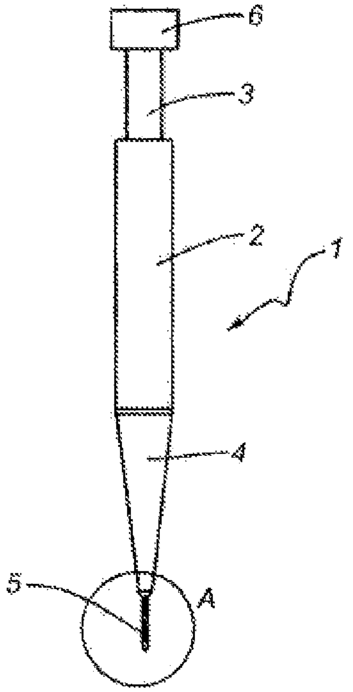
Fig. 1A (Prior Art)
FIG. 1A is a front view of a hair graft implanting instrument in a patient's scalp, commonly used in prior art, with its needle in an exterior position.
Figure 1B:
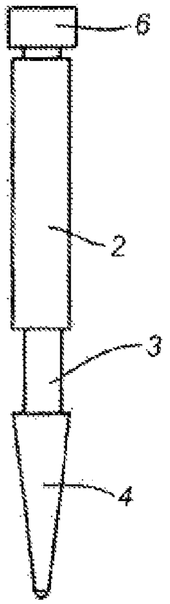
Fig. 1B (Prior Art)
FIG. 1B is a front view of the hair graft implanting instrument from FIG. 1A with its needle in a retracted position.
Figure 2:
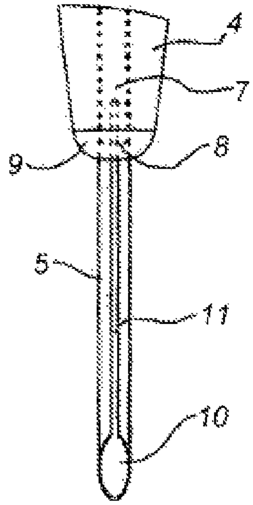
Fig. 2 (Prior Art)
FIG. 2 is an enlarged view of the details of zone A from FIG. 1A.

In FIGS. 1A, 1B, and 2, it can be seen that hair graft implanting instrument 1 comprises an elongated body with a sleeve 2 in cylindrical form in which slides a piston 3 extended at one of its ends by a cone-shaped tapered part 4, and at its opposite end by a switch actuator 6.

The sleeve 2 is positioned between the cone-shaped tapered part 4 and the actuator switch 6, and has a length of less than the distance between the cone-shaped tapered part 4 and the actuator switch 6, so as to allow the piston 3 to slide in relation to the sleeve 2.

The cone-shaped tapered part 4 has a base width substantially identical to that of the sleeve, and a rounded tip 9.

A hollow implanting needle 5, of cylindrical form, suitable for containing a hair graft 12 (FIGS. 3A to 3C) is solidly attached to the sleeve 2 by coupling means (not shown). The needle 5 is mobile between a retracted position (FIG. 1B) inside the cone-shaped tapered part 4 of the piston 3 when the latter is mobilized in relation to the sleeve 2 by means of the actuator switch 6, and a deployed position (FIG. 1A) wherein it is in projection from the tapered part 4 of the piston 3. The length L of the implanting needle 5 in projection is in the range of 8 to 10 mm.

A sliding rod 7 in cylindrical form is positioned on the inside of the hollow needle 5.

The sliding rod 7, with a diameter substantially inferior to the inside diameter of the needle 5, is attached in solidarity to the piston 3 by its proximal end, close to the actuator switch 6, by coupling means (not shown), and has an opposite free distal end 8, positioned at the height of the tip 9 of the cone-shaped tapered part 4, in such a way that it may serve as end stop and release a hair graft (not shown) from the needle 5 when the latter is withdrawn from the inside of the piston 3.

Figure 3A:
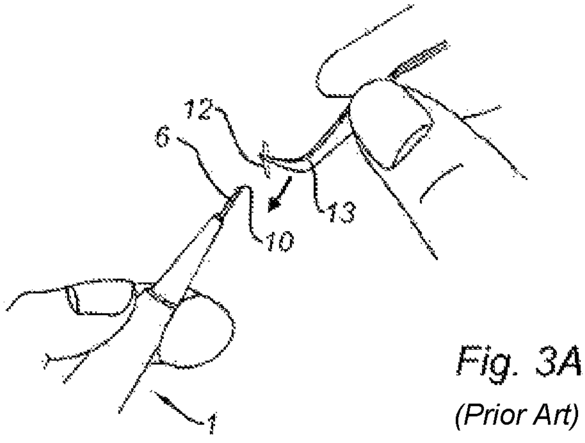
Fig. 3A (Prior Art)
FIGS. 3A to 3C are perspective views of the different steps, in prior art, of manually loading a hair graft into an implanting instrument, according the FIG. 1A.
Figure 3B:
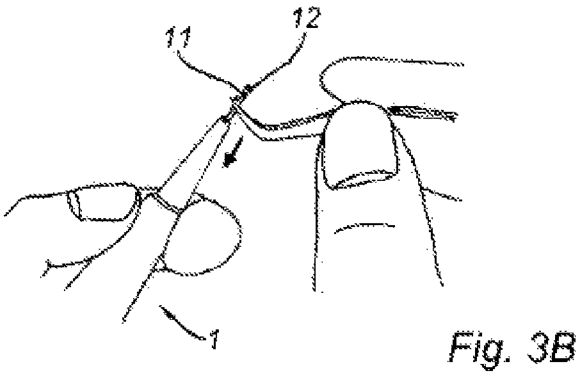
Fig. 3B (Prior Art)
Figure 3C:
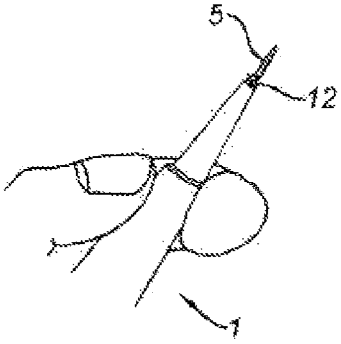
Fig. 3C (Prior Art)

The hollow needle 5 has a beveled, sharp, free end 10 suitable for penetrating the skin as well as, along a part of its length, a thin longitudinal opening or slot 11 enabling the insertion of a hair graft 12 generally by threading or traction with tweezers 13, as illustrated in FIGS. 3A to 3C.

In FIG. 3A, we see that the hair graft 12 is manually seized by it upper part between the jaws of a pair of thin tweezers 13 held by an operator. The hair graft 12 is brought closer in respect of the free end 10 of the hollow implanting needle 5 of the implanting instrument 1. The hair graft 12 is then inserted inside the hollow needle 5 through the slot 11, very delicately by traction or threading, until the hair graft is totally loaded and lodged as illustrated in FIGS. 3B and 3C. The implanting instrument 1 is now ready to be used for the implantation of the hair graft 12 into the skin.

It can easily be understood that the step of manually loading the hair graft into the implanting needle is a long and delicate maneuver requiring extreme precision that prolongs the operation time. Indeed, the needle 5 is generally made of stainless steel, and has very small dimension: 10 millimeters in length on its free part, an outside diameter in the range of 0.7 mm to 1 millimeter, and a very thin wall thickness of 0.1 mm. The needle is open all along its free length by a slot 11 whose width is 0.2 mm, over a length of approximately 10 mm starting at the posterior edge of the beveled tip 10 of the needle 5. Thus, it is necessary for the operator to correctly visualize and position the slot 11 in order to very delicately, manually insert the hair graft seized by the tweezers 13.

It can easily be understood that even a small part of the hair graft 12 might end up on the outside of the needle 5 through the slot 11 and could be severed by strangulation in the slot 11 due to its narrowness when positioned inside the needle 5, rendering the hair graft improper for implantation.

Figure 4A:
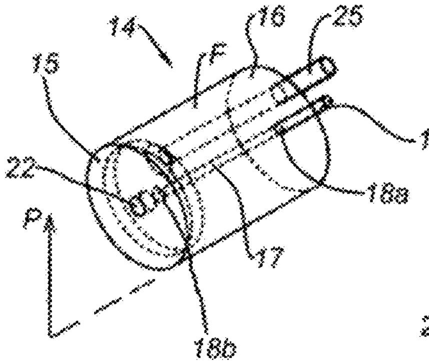
FIGS. 4A and 4B are perspective views of the hair graft loading device according to the invention.
Figure 4B:
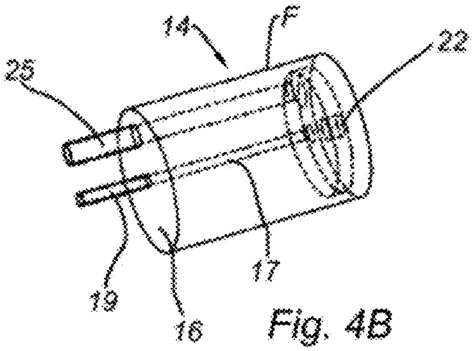
Figure 5:
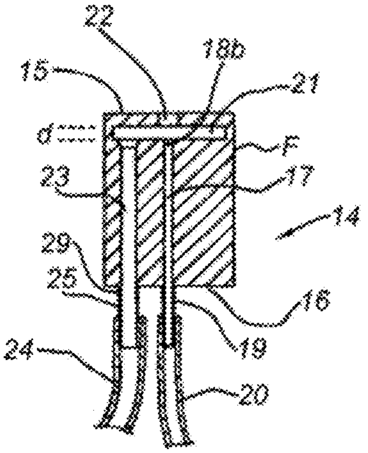
FIG. 5 is a sectional view of the device of FIG. 4A, according to frame P designated on FIG. 4A.

FIGS. 4A, 4B and 5 are respectively perspective views and sectional views of a hair graft loading device 14 according to an embodiment of the present invention.

The hair graft loading device 14 has a cylindrical form, a length of approximately 20 mm and a diameter of approximately 16 mm. It has a flat proximal side 15, a flat distal side 16 and a longitudinal side F connecting the proximal 15 and distal 16 sides.

The hair graft loading device 14 comprises a circular-shaped chamber 21 arranged near the proximal side 15. It further consists of a cylindrical-form rectilinear longitudinal central channel 17 that has a first hole 18*a* leading from the distal side 16, and an opening 18*b* opposite of the first hole 18*a*, leading to the chamber 21.

The proximal side 15 comprises a second hole 22 that opens into the chamber 21. The second hole 22 can receive, in a sealed manner, the needle 5 (not shown) of an implanting instrument as described above, said needle being able to cross the chamber 21 to reach the central channel 17.

In this way, the central channel 17 is capable of axially receiving, over a part of its length, the needle of an implanting instrument as described in respect to FIGS. 1A, 1B, and 2, inserted through the central hole 22.

Figures 7A, 7B, 7C, 7D, 7E:
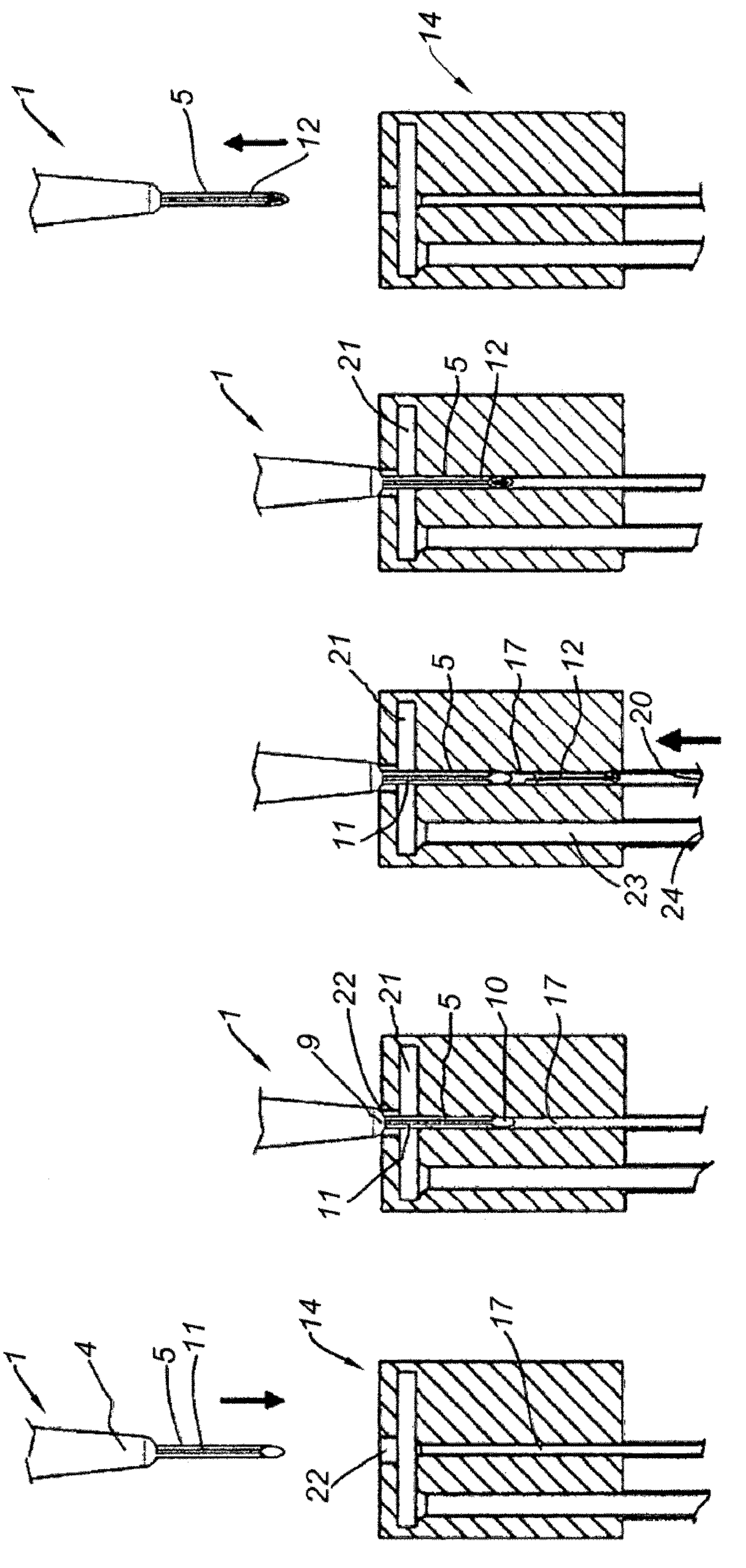
FIGS. 7A to 7E are sectional views illustrating the different successive steps of loading a hair graft into the needle of an implanting instrument according to FIG. 1A, using the device according to the invention.

The central channel 17 has an outward projection, at its first hole 18*a*, a sealed connection means 19 to the first flexible tubing 20 (FIG. 5) of variable length and having an inside diameter of approximately 1 to 1.2 mm suitable to contain and deliver a hair graft 12 (FIGS. 7C to 7E).

The chamber 21 communicates with the remotely situated vacuum source through a vacuum conduit 23 comprising an outlet orifice 29 leading to the distal side 16 and connected to a second tubing 24 (FIG. 5) by a connection means 25.

The chamber 21 has a height "d" of approximately 1.5 mm, sufficient enough to provide an easy passage for fluids (air or water) between the central channel 17 and the lateral channel 23, and sufficiently narrow as to allow the full loading of a hair graft into the needle 5 of an implanting instrument, as described above in respect of FIGS. 1 to 2, during its insertion into the central channel 17 via the second hole 22, as it shall be described in detail in respect of FIGS. 7A to 7E.

The second hole 22 of the hair graft loading device 14 has a diameter sufficiently large to easily insert the needle 5 of the implanting instrument and sufficiently narrow to form an end stop and a watertight seal with the tip 9 of the implanting instrument as described above.

Figure 6:
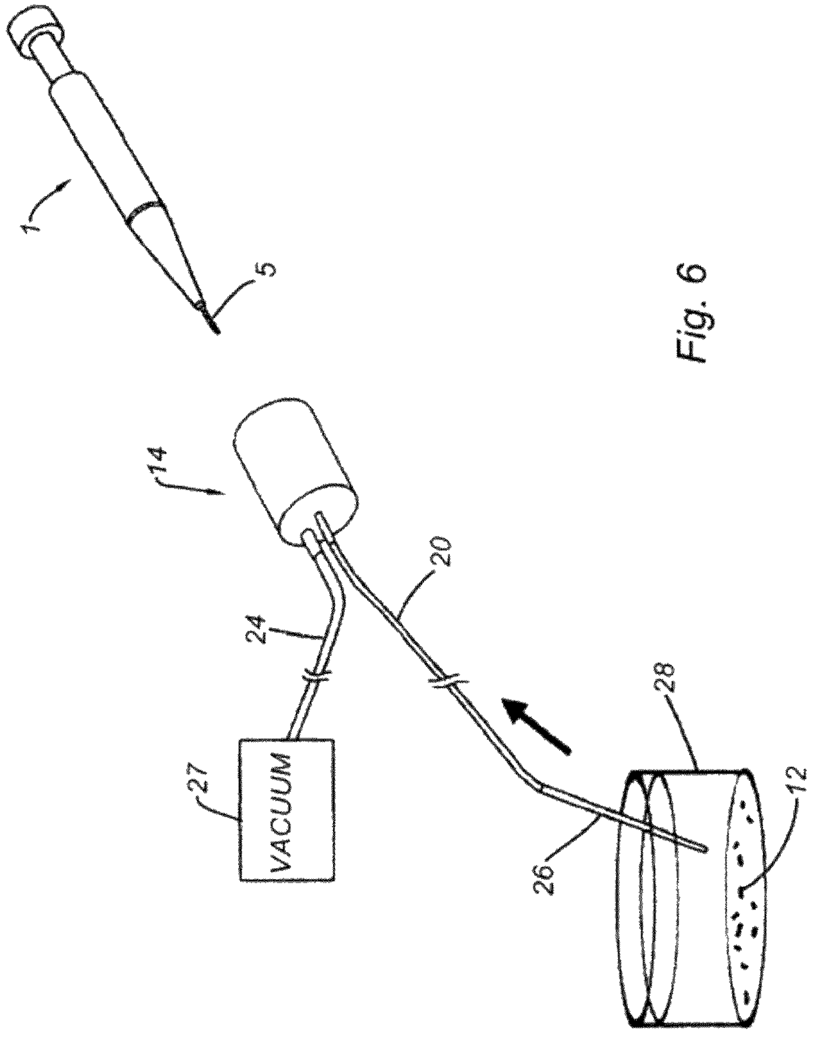
FIG. 6 is a perspective view illustrating a method of embodiment of loading a hair graft into an implanting instrument according to FIGS. 1A, 1B, and 2, using the device according to the invention.

FIG. 6 prospectively illustrates a method of use for the hair graft loading device 14 of the present invention.

The hair graft loading device 14, capable of being attached for example to a ring on the operator's finger (not shown), is connected by the first tubing 20 to a rigid tube 26, for example in stainless steel, of an inside diameter of approximately 1 to 1.2 mm, sufficient for allowing the passage of a hair graft 12.

The free end of the tube 26 is intended to be brought into contact with the epidermic part of the hair graft 12 soaking among other hair grafts in the bottom of a hair graft container or tank 28 previously filled with physiological serum or another preservation liquid, in view of its suction into the hair graft loading device 14.

The hair graft loading device 14 is also connected by a second tubing 24 to a vacuum source 27 that can be actuated by an operator. The implanting instrument 1, described in FIG. 1, is positioned axially in front of the hair graft loading device 14, ready to receive a hair graft 12 as described below.

In this method of use, the suction of a hair graft 12 into the hair graft loading device 14 is done manually by an operator that manipulates the tube 26 in order to bring it into contact with the epidermic part of the hair graft 12.

FIGS. 7A to 7E are sectional views illustrating the different steps of loading a hair graft 12 into the needle 5 of an implanting instrument 1 using the hair graft loading device 14 according to the invention.

In FIGS. 7A and 7B, the needle 5 of the implanting instrument 1 is aligned in the axis of the central channel 17 in respect to the second hole 22 of the hair graft loading device 14. The implanting needle 5 is then frictionally inserted into the central channel 17 until the tip 9 of the implanting instrument 1 comes up against the circular edge of the second hole 22, forming a circular fluid-tight seal.

In the coupling position between the implanting instrument 1 and hair graft loading device 14, the implanting needle 5 forms a cylindrical open space at its free end 10 in the continuation of the central channel 17 and laterally open in the chamber 21 through the free end of the slot 11.

In reference to FIGS. 7C and 7D, vacuuming via the vacuuming source 27, controlled by an operator, from the chamber 21 via the conduit 23 and the second tubing 24, provokes a vacuum successively in the chamber 21, in the needle 5 via the free portion of the slot 11, in the central channel 17, in the first tubing 20 and in the tube 26 (FIG. 6) situated in respect to the epidermal part of a hair graft 12, provoking its suction and its movement in a fraction of a second to the central channel 17 to be inserted and blocked inside the needle 5 in respect to the chamber 21, taking into account the fact that the width of the slot 11 of approximately 0.2 mm is sufficiently wide in order to allow fluids to pass, but sufficiently narrow to block and immobilize the hair graft whose diameter is larger by approximately 0.9 to 1 mm.

Once the hair graft 12 is loaded and positioned inside the needle 5 of the implanting instrument 1, the latter is then separated by traction from the hair graft loading device 14, as shown in FIG. 7E, for the purpose of its final use of implantation of the hair graft into the skin or the scalp of a patient.

The implanting instrument 1, freed of the hair graft 12, is once again inserted into the hair graft loading device 14 in order to load a second hair graft, and so on.

It is also possible to have several devices 14 whose central channel 17 diameter varies to adapt to the outside diameter of the needle of the implanting instrument to be loaded, for example 0.8, or 0.9, or 1 mm in diameter, according to the size of the hair grafts. Such devices are quickly interchangeable by the operator during an operation.

The hair graft loading device 14 according to the invention may be easily manufactured in a transparent, rigid, plastic material such as polycarbonate or methyl methacrylate, by injection into a mold or by machining and gluing.

Figure 8:
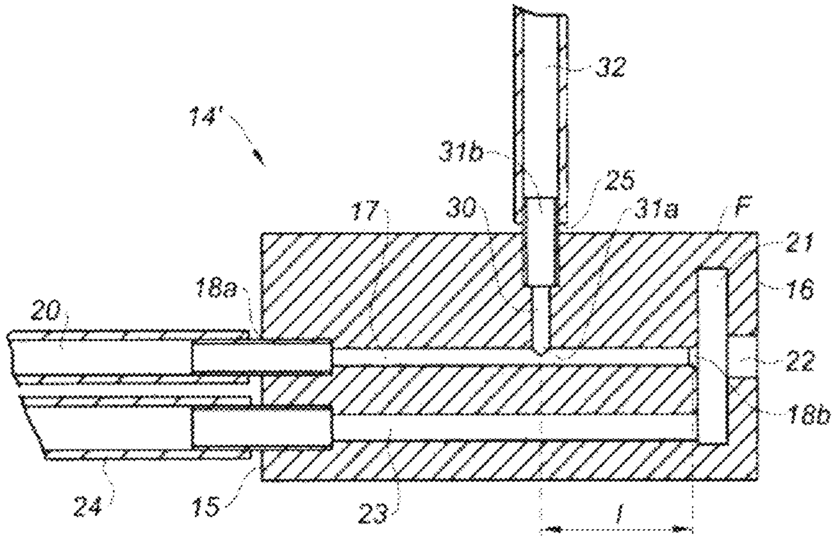
FIG. 8 is a sectional view illustrating another embodiment of the hair graft loading device.

FIG. 8 is a sectional view of the hair graft loading device 14' according to another embodiment.

Unlike the hair graft loading device 14 according to the embodiment in FIGS. 4A, 4B and 5, the hair graft loading device 14' in FIG. 8 has an accessory channel 30 leading perpendicularly from the longitudinal side F of the device, into the central channel 17.

The accessory channel 30 comprises an accessory hole 31*a* leading to the central channel 17 and an accessory opening 31*b* opposite of the accessory hole 31*a* and positioned in the longitudinal side F of the device.

The accessory hole 31*a* is located at a distance "1" from the opening 18*b* of the central channel 17 leading into the chamber 21. The distance "1" is equal to the length L of the implanting needle 5 of an implanting instrument as describe in respect of FIGS. 1A, 1B, and 2.

The accessory channel 30 has a diameter substantially identical to the diameter of the central channel 17.

Figure 9:
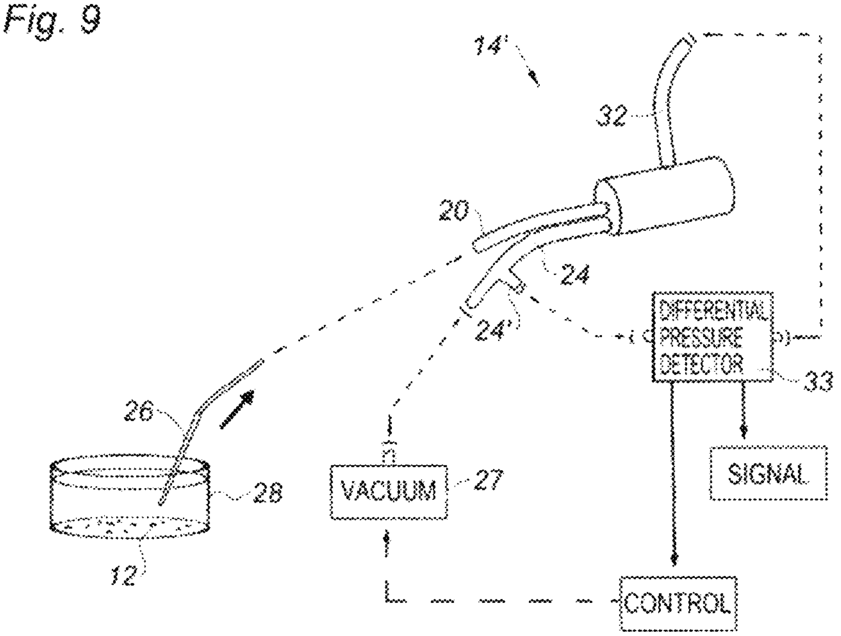
FIG. 9 is a perspective view illustrating a method of use of the device in FIG. 8.

Furthermore, the accessory channel 30 has an outward projection, on its accessory opening 31*b*, a means of sealed connection 25 to a third tubing 32 configured to be connected to a pressure detector 33 (FIG. 9).

As shown in FIG. 9, the pressure detector 33 is also connected to a second tubing 24 enabling the connection of the hair graft loading device 14' to the vacuum source 27. The link between the pressure detector 33 and the second tubing 24 is made via a cannula 24'.

In this way, the pressure detector 33 is able to detect a brutal variation in pressure between the accessory hole 31*a* and the vacuum source 27. Such a variation may be provoked by the obstruction of the implanting needle 5 by a hair graft 12 sucked into the rigid tube 26 of the tubing 20, according to the loading steps for a hair graft described in respect to FIGS. 7C and 7D.

The pressure detector 33 is assimilated to a pneumatic contactor. It indicates to the operator, by a sound or light signal, the presence of the hair graft in the implanting needle 5.

In this method of use, the suction of a hair graft 12 into the hair graft loading device 14' is done manually by an operator that manipulates the tube 26 in order to bring it into contact with the epidermal part of a hair graft 12 positioned in a tank 28.

FIG. 10 illustrates a hair graft storage tray 34 according to the invention.

The storage tray 34 is rectangular, with a length of 20 cm, a width of 10 cm and a height of 1 cm. It comprises fifteen rows of thirty-five wells 35 configured to contain a hair well each 12 (not shown). The wells 35 are cylindrical, aligned, equidistant from each other, and spaced at approximately 5 mm.

Each well has a diameter of 1.5 mm and a depth of 8 mm. These dimensions make it possible to maintain the hair graft in a given position, adapted to allow the suction of the hair graft into the hair graft loading device 14, 14' as described above.

The storage tray 34 is configured to be placed in a slightly larger tank 28 (FIG. 13), comprising a physiological serum.

FIG. 11 illustrates an embodiment of a hair graft suction device 100 configured to suck a hair graft 12 located in a hair graft tank 28, and insert it into a hair graft loading device 14, 14' as described above.

The hair graft suction device 100 is a robot comprising a support 101 for a housing 102 of a rigid tube 26 configured to be connected to the first tubing 20 of a hair graft loading device 14, 14' as described above, the housing 102 being configured to be moved along three orthogonal axes, respectively the axis of length x, the axis of depth y and the axis of height z, using rails 103 positioned on the support 101.

The support 101 comprises a base 104 of a longitudinal axis corresponding to the axis of length x, in an L form, comprising two branches, respectively horizontal 104' and vertical 104". The horizontal branch 104' extends according to the axis of depth y and the vertical branch 104" extends according to the axis of height z.

The support further comprises two arms, respectively horizontal 105 and vertical 106.

The horizontal arm 105 extends from the vertical branch 104" on the base, parallel to the horizontal branch 104' and vertically aligned with it. It is configured to be moved along the axis of length x, via rails extending along the axis of length x on the vertical branch 104" of the base.

The vertical arm 106 extends perpendicularly to the horizontal arm 105, along the axis of height z. It is connected to the horizontal arm 105 via rails 103 extending along the axis of depth y on the horizontal arm 105, so as to be mobile along the axis of depth y.

The housing 102 is connected to the vertical arm 106 via rails 103 extending along the axis of height z on the vertical arm 106, so as to be mobile along the axis of height z.

The tube 26 extends along the axis of height z. It has a free low end 26' and a high end 26" configured to be connected to the first tubing 20 of a hair graft loading device 14, 14' as described above, as represented in FIG. 13.

The support allows the housing 102 to be moved along the orthogonal axes of length x, depth y, and height z, in order to position the low end 26' of the tube 26 in contact with the epidermic part of a hair graft 12 located in a tank 28 positioned on a horizontal branch 104' of the base 104 of the support 101.

Figure 13:
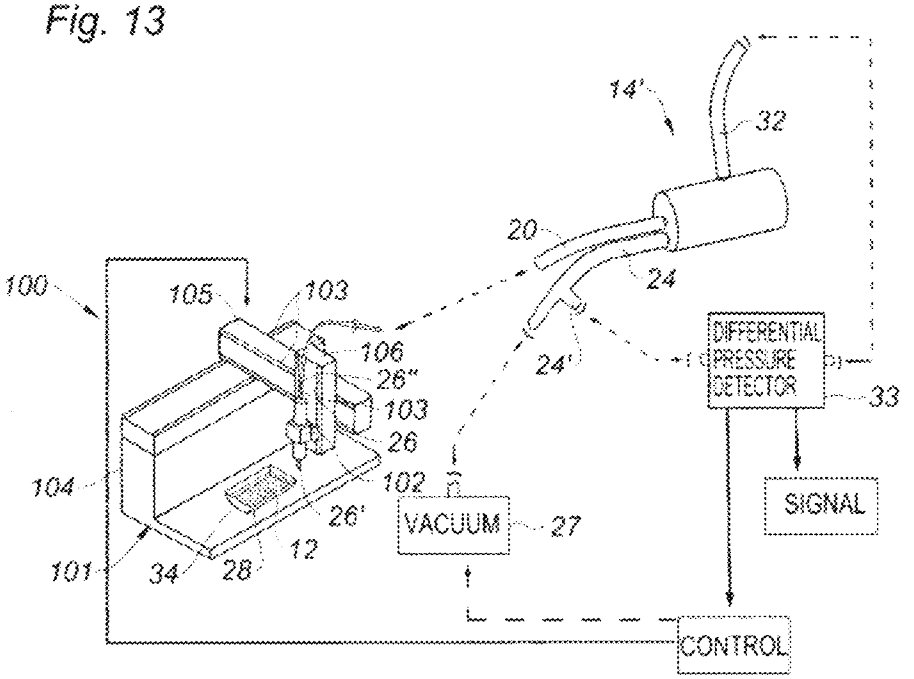
FIG. 13 is a perspective view illustrating a method of use for the device in FIG. 11.

As it will be seen in the FIG. 13, the suction of a hair graft 12 into the hair graft loading device 14 is carried out mechanically by the hair graft suction device 100.

FIG. 12 illustrates another embodiment of a hair graft suction device 100'.

Unlike the embodiment in FIG. 11, the hair graft suction device 100' comprises a camera 107 configured to record an image of a hair graft located in a tank 28 positioned on a horizontal branch 104' of the base 104 of the support 101, and a controller 108 configured to analyze the precise position of the hair graft 12.

In this embodiment, the movement of the housing 102 allowing the tube 26 to be brought into contact with the epidermal part of the hair graft 12, is carried out automatically via the detection of the position of a hair graft 12 in the tank 28.

FIG. 13 illustrates a method of use of a hair graft suction device 100 from FIG. 11, in a hair graft loading device 14' from FIG. 8.

Unlike the method described in respect of FIG. 9, the suction of a hair graft 12 into the hair graft loading device 14' is carried out mechanically by the hair graft suction device 100.

Furthermore, the hair grafts 12 are positioned in a storage tray 34 as described in respect of FIG. 10, in order to allow an automatic suction of the hair graft. Indeed, the hair grafts are positioned in the wells 35 (FIG. 10) of the storage tray 34, in a position adapted to their suction into the hair graft loading device 14.

Thus, the movements of the housing 102 are predefined according to the distance between the wells.

The movements of the housing 102 are controlled by the pressure detector 33. The pressure detector thus allows the automatic control of the movement of the tube 26 in respect to a hair graft according to the preprogrammed path.

In a variant according to which the hair grafts are located in a tank 28, without a storage tray, the movement of the housing 102 is carried out manually by an operator to bring the tube 26 into contact with the epidermal part of a hair graft 12 located in the tank 28.

In a non-represented variant, the suction device 100 is used to suck a hair graft 12 into a hair graft loading device 14 according to the FIGS. 4A, 4B, and 5.

In this variant, the hair graft suction is actuated by an operator, using a pedal (not shown). The movement of the housing 102 is carried out when the operator releases the pedal.

Figure 14:
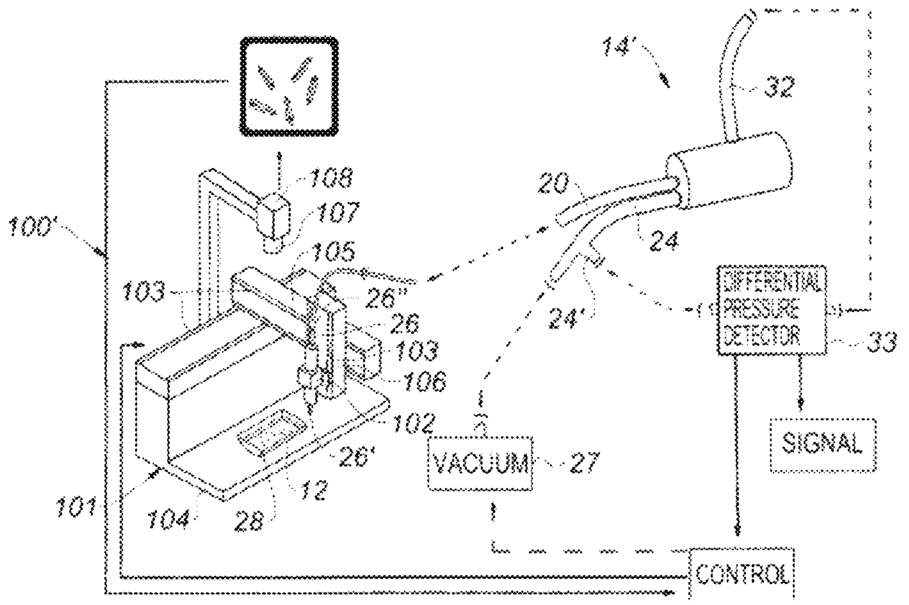
FIG. 14 is a perspective view illustrating a method of use for the device in FIG. 12.

FIG. 14 represents a method of use for a hair graft suction device 100' from FIG. 12, in a hair graft loading device 14' from FIG. 8.

Unlike the method described in respect of FIG. 9, the suction of a hair graft 12 into the hair graft loading device 14' is carried out mechanically by the hair graft suction device 100'.

Furthermore, the suction is carried out automatically via the detection of the position of the hair grafts by the camera 107 and the controller 108.

In a non-represented variant, the suction device 100' is used to suck a hair graft 12 into a hair graft loading device 14 according to the FIGS. 4A, 4B, and 5.

Although the hair graft loading device was described as having a cylindrical form, it is possible that it have a flattened cubic or parallelepipedic form having a transparent convex magnifying-type side in order to better visualize the central channel and the insertion of the hair graft into the implanting needle.

Although the hair graft suction device has been described with the use of a Cartesian-type support, the use in the same manner of a SCARA-type support (Selective Compliance Assembly Robot Arm) or a five- or six-axis articulated support is easily imaginable.

The embodiments illustrated and discussed in this specification are intended only to teach those skilled in the art how to make and use the disclosure herein. In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. A loading device for loading a hair graft into an implanting instrument which is separate and distinct from the loading device, wherein the loading device is contactable by the implanting instrument for loading of a hair graft extracted from a donor region of skin, and wherein the loading device is further constructed to be separable from the implanting instrument at a time when the implanting instrument is used to implant the loaded hair graft into a recipient region of skin, and wherein the implanting instrument has a slotted needle having an elongate slot extending lengthwise therealong and into which the extracted hair graft is loadable into the needle and implantable from the needle into the recipient region of skin, the loading device comprising:

a first hole connected to a central channel leading into a fluid discharge chamber, the central channel extending across a majority of a length of the loading device, wherein the fluid discharge chamber is perpendicular to the central channel;

a second hole communicating with the fluid discharge chamber and defining a path with the central channel so as to allow the slotted needle of the implanting instrument to be inserted into said path through the second hole with the slot of the slotted needle communicable with the fluid discharge chamber, the second hole having a diameter sized to receive the slotted needle of the implanting instrument and form an end stop and a watertight seal with a tip of the implanting instrument, wherein the second hole is positioned opposite to the first hole and extends into a center of the fluid discharge chamber; and connection means from the fluid discharge chamber to a vacuum source, the connection means including a vacuum conduit that extends across the majority of the length of the loading device, wherein the vacuum conduit is parallel to the central channel, wherein the fluid discharge chamber is perpendicular to the vacuum conduit;

the first hole being constructed to be brought into communication with a first tubing so as to deliver a hair graft such that the hair graft can be loaded into the needle of the implanting instrument by suction applied by the fluid discharge chamber to the slot of the slotted needle, the first hole configured to pass fluid from the first tubing to transport the hair graft to the loading device;

wherein the fluid discharge chamber has a height of approximately 1.5 mm.

2. The loading device according to claim 1, wherein the fluid discharge chamber has dimensions such that the fluid discharge chamber is able to allow both a passage of fluid, inclusive of air or water, between the central channel and the connection means of the fluid discharge chamber, and the loading of a hair graft into the needle of the implanting instrument, inserted into the central channel via the second hole.

3. The loading device according to claim 1, wherein the central channel is rectilinear.

4. The loading device according to claim 1, wherein the connection means of the fluid discharge chamber is intended to be connected to the vacuum source via an outlet hole.

5. The loading device according to claim 1, having a substantially cylindrical form with a proximal side, a distal side, and a longitudinal side connecting the proximal and the distal sides.

6. The loading device according to claim 5, wherein the proximal side comprises the second hole, and the distal side comprises the first hole of the central channel.

7. The loading device according to claim 1, wherein the first hole and the second hole are aligned in a longitudinal axis of the central channel.

8. The loading device according to claim 1, wherein the first tubing connects the central channel to a hair graft tank and the connection means connects the fluid discharge chamber to the vacuum source.

9. A storage tray for hair grafts configured to facilitate the suction of a hair graft into the loading device according to claim 1, the storage tray comprising at least one well configured to contain a hair graft and whose dimensions allow maintenance of the hair graft in a given position enabling the suction of the hair graft into the loading device.

10. A hair graft suction device configured to insert a hair graft into the loading device according to claim 1, the suction device comprising a support and a housing for a rigid tube configured to be connected to the first tubing of the loading device, the housing being mobile in relation to the support and configured so as to be moved in order to bring the rigid tube into contact with a hair graft.

11. The hair graft suction device according to claim 10, comprising:

a camera configured to record an image of the hair graft located in a container, and a controller configured to analyze a precise position of the hair graft.

12. An assembly comprising the loading device according to claim 1 and a hair graft suction device, wherein the hair graft suction device comprises a support and a housing for a rigid tube configured to be connected to the first tubing of the loading device, the housing being mobile in relation to the support and configured so as to be moved in order to bring the rigid tube into contact with a hair graft.

13. An assembly comprising the loading device according to claim 1, a hair graft suction device, and a storage tray, wherein the hair graft suction device comprises a support and a housing for a rigid tube configured to be connected to the first tubing of the loading device, the housing being mobile in relation to the support and configured so as to be moved in order to bring the rigid tube into contact with a hair graft, and wherein the storage tray comprises at least one well configured to contain the hair graft and whose dimensions allow maintenance of the hair graft in a given position enabling the suction of the hair graft into the loading device.

14. The loading device according to claim 1, further comprising an accessory channel opening perpendicularly from a longitudinal face of the loading device into the central channel;

the accessory channel having an accessory hole opening into the central channel and an accessory opening opposite the accessory hole and positioned in the longitudinal face of the loading device, and the accessory channel having, projecting outwards at the accessory opening, a sealed connection means for sealed connection to a third tubing configured to be connected to a pressure sensor.

15. The loading device according to claim 1, wherein the loading device is constructed to be worn on a first hand of an operator while the implanting instrument is handled by a second hand of the operator.

16. A method of use of an implanting instrument and a loading device for loading hair grafts into the implanting instrument which is separate and distinct from the loading device, wherein the loading device is contactable by the implanting instrument for loading of a hair graft extracted from a donor region of skin, and wherein the loading device is further constructed to be separable from the implanting instrument at a time when the implanting instrument is used to implant the loaded hair graft into a recipient region of skin, and wherein the implanting instrument has a slotted needle having an elongate slot extending lengthwise therealong and into which the extracted hair graft is loadable into the needle and implantable from the needle into the recipient region of skin, wherein the loading device includes:

a first hole connected to a central channel leading into a fluid discharge chamber;

a second hole communicating with the fluid discharge chamber and defining a path with the central channel so as to allow the slotted needle of the implanting instrument to be inserted into said path through the second hole with the slot of the slotted needle communicable with the fluid discharge chamber, the second hole having a diameter sized to receive the slotted needle of the implanting instrument and form an end stop and a watertight seal with a tip of the implanting instrument; and connection means from the fluid discharge chamber to a vacuum source;

the first hole being constructed to be brought into communication with a first tubing so as to deliver a hair graft such that the hair graft can be loaded into the needle of the implanting instrument by suction applied by the fluid discharge chamber to the slot of the slotted needle, wherein the fluid discharge chamber has a height of approximately 1.5 mm, wherein the method of use comprises:

connecting the first tubing to the first hole, inserting the needle of the implanting instrument, in a sealed manner, into the second hole, in such a way that it penetrates into at least part of the central channel with the slot of the slotted needle being communicable with the fluid discharge chamber, bringing a free end of the first tubing into contact with the hair graft located in a solution in a tank, vacuum sealing the fluid discharge chamber, whereby the hair graft is loaded into the needle of the implanting instrument by suction applied by the fluid discharge chamber to the slot of the slotted needle, and separating the implanting instrument from the loading device in preparation for implantation of the loaded hair graft from the needle into the recipient region of skin.

17. The method according to claim 16, wherein the loading device further includes an accessory channel opening perpendicularly from a longitudinal face of the loading device into the central channel;

the accessory channel having an accessory hole opening into the central channel and an accessory opening opposite the accessory hole and positioned in the longitudinal face of the loading device, and the accessory channel having, projecting outwards at the accessory opening, a sealed connection means for sealed connection to a third tubing configured to be connected to a pressure sensor, wherein the method further comprises confirming that the hair graft is present and has been loaded into the implanting instrument by reference to the pressure sensor.

18. The method according to claim 16, wherein the loading device is constructed to be worn on a first hand of an operator while the implanting instrument is handled by a second hand of the operator.

19. A system comprising a loading device distinct from a separate implanting instrument, the system being constructed for loading a hair graft extracted from a donor region of skin from the loading device into the implanting instrument, and further being constructed for implanting the loaded hair graft into a recipient region of skin, wherein the implanting instrument comprises a slotted needle having an elongate slot extending lengthwise therealong and into which the extracted hair graft is loadable into the needle and by which the loaded hair graft is implantable from the needle into the recipient region of skin, and wherein the loading device comprises:

a first hole connected to a central channel leading into a fluid discharge chamber;

a second hole communicating with the fluid discharge chamber and defining a path with the central channel so as to allow the slotted needle of the implanting instrument to be inserted into said path through the second hole with the slot of the slotted needle communicable with the fluid discharge chamber; and connection means from the fluid discharge chamber to a vacuum source;

the first hole being constructed to be brought into communication with a first tubing so as to deliver a hair graft such that the hair graft can be loaded into the needle of the implanting instrument by suction applied by the fluid discharge chamber to the slot of the slotted needle.

20. The system according to claim 19, wherein the fluid discharge chamber has a height of approximately 1.5 mm.

21. The system according to claim 19, wherein the loading device is constructed to be worn on a first hand of an operator while the implanting instrument is handled by a second hand of the operator.

* * * * *